US012059327B2

(12) United States Patent
Gallien et al.

(10) Patent No.: US 12,059,327 B2
(45) Date of Patent: Aug. 13, 2024

(54) ITEM OF CLOTHING FOR THE TREATMENT OF SKIN AND SUBCUTANEOUS TISSUE DISORDERS AND SPORTS RECOVERY, COMPRISING A TUBULAR BODY

(71) Applicant: THUASNE, Levallois Perret (FR)

(72) Inventors: Nathalie Gallien, Saint-Etienne (FR); Henri De Moncuit, Bakersfield, CA (US); Reynald Convert, Lyons (FR)

(73) Assignee: THUASNE, Levallois Perret (FR)

( * ) Notice: Subject to any disclaimer, the term of this patent is extended or adjusted under 35 U.S.C. 154(b) by 1086 days.

(21) Appl. No.: 15/301,773

(22) PCT Filed: Apr. 3, 2015

(86) PCT No.: PCT/EP2015/097006
§ 371 (c)(1),
(2) Date: Oct. 4, 2016

(87) PCT Pub. No.: WO2015/155372
PCT Pub. Date: Oct. 15, 2015

(65) Prior Publication Data
US 2017/0119585 A1 May 4, 2017

(30) Foreign Application Priority Data

Apr. 9, 2014 (FR) ..................... 14 53171

(51) Int. Cl.
*A61F 13/08* (2006.01)
*A61F 13/06* (2006.01)
(Continued)

(52) U.S. Cl.
CPC .......... *A61F 13/085* (2013.01); *A61F 13/062* (2013.01); *A61F 13/102* (2013.01); *A61F 13/14* (2013.01)

(58) Field of Classification Search
CPC .......... A61F 5/0109; A61F 5/02; A61F 5/024; A61F 5/028; A61F 5/03; A61F 13/062;
(Continued)

(56) References Cited

U.S. PATENT DOCUMENTS 2,343,477 A * 3/1944 Ross .................. A43B 3/04
36/10
5,711,031 A * 1/1998 Clement .............. A41D 13/012
2/82

(Continued)

FOREIGN PATENT DOCUMENTS

CN 1354643 6/2002
CN 102596133 7/2012
(Continued)

OTHER PUBLICATIONS

International Search Report, dated May 29, 2015, from corresponding PCT application.
(Continued)

*Primary Examiner* — Ophelia A Hawthorne
(74) *Attorney, Agent, or Firm* — NIXON & VANDERHYE

(57) ABSTRACT

An item of clothing for treating skin and subcutaneous tissue disorders, includes a tubular body with at least one relatively inelastic part having an inner layer defining an inner face of the inelastic part, the inner layer including a plurality of protruding spaced apart elements. A relatively elastic part extends from a first axial end to an opposite axial end of the tubular body and connects a first edge of the inelastic part to a second edge of the inelastic part. The item further includes: a flap which is relatively inelastic and has an inner layer defining an inner face of the flap, the inner layer including a plurality of protruding spaced apart elements, the flap being secured to at least part of the first edge of the inelastic
(Continued)

part, and a device for reversibly attaching the flap to at least part of the second edge of the inelastic part.

20 Claims, 5 Drawing Sheets

(51) Int. Cl.
*A61F 13/10* (2006.01)
*A61F 13/14* (2006.01)

(58) Field of Classification Search
CPC ...... A61F 13/069; A61F 13/08; A61F 13/085; A61F 13/10; A61F 13/101; A61F 13/102; A61F 13/104; A61F 13/105; A61F 13/107; A61F 13/108; A61F 13/14; A61F 13/143; A61F 13/145; A61F 13/146; A61F 13/148; A61F 5/01; A61F 5/30; A61F 5/132; A61F 5/134; A61F 5/0118; A41C 1/02; A41C 1/08; A41C 1/10; A41C 3/02; A41D 13/08; A41D 13/081; A41D 13/082; A41D 13/084; A41D 17/00; A41D 17/02; A41D 17/005; A41D 2300/30; A41D 2600/10; A41F 1/00; A41F 1/006; A41F 1/04
USPC ........................................................ 602/63, 78
See application file for complete search history.

(56) References Cited

U.S. PATENT DOCUMENTS

| | | | |
|---|---|---|---|
| 5,743,866 A * | 4/1998 | Bauerfeind | ........... A61F 5/0125 602/62 |
| 5,918,602 A * | 7/1999 | Shaw | .................... A61F 13/062 128/882 |
| 6,186,966 B1 | 2/2001 | Grim et al. | |
| 6,592,539 B1 | 7/2003 | Einarsson et al. | |
| 7,748,056 B2 | 7/2010 | Mickle | |
| 9,387,146 B2 | 7/2016 | Avitable et al. | |
| 9,833,351 B2 | 12/2017 | Arbesman et al. | |
| 2005/0113729 A1* | 5/2005 | Scott | ...................... A61F 13/085 602/19 |
| 2006/0211968 A1 | 9/2006 | Gordon, Jr. et al. | |
| 2010/0064415 A1* | 3/2010 | Melhart | .............. A41D 13/0015 2/125 |
| 2011/0208149 A1* | 8/2011 | Vastag | .............. A61F 13/49012 604/385.16 |
| 2012/0010547 A1* | 1/2012 | Hinds | .................. A61F 5/05866 602/21 |
| 2012/0109031 A1* | 5/2012 | Vollbrecht | ............ A61F 13/062 602/5 |
| 2015/0073317 A1* | 3/2015 | Cox | .......................... A61F 5/30 601/84 |
| 2015/0209217 A1 | 7/2015 | Chardon-Bras et al. | |

FOREIGN PATENT DOCUMENTS

| | | |
|---|---|---|
| CN | 203458532 | 3/2014 |
| EP | 1 926 458 B1 | 2/2011 |
| ES | 2344379 | 8/2010 |
| JP | S56-146938 | 11/1981 |
| JP | H07-5613 | 1/1995 |
| JP | 2002-516713 | 6/2002 |
| JP | 2002-345866 | 12/2002 |
| JP | 2010-518895 | 6/2010 |
| WO | 99/62440 | 12/1999 |
| WO | 2008/101314 | 8/2008 |

OTHER PUBLICATIONS

FR Search Report, dated Jan. 23, 2015, from corresponding FR application.

* cited by examiner

ITEM OF CLOTHING FOR THE TREATMENT OF SKIN AND SUBCUTANEOUS TISSUE DISORDERS AND SPORTS RECOVERY, COMPRISING A TUBULAR BODY

BACKGROUND OF THE INVENTION

Field of the Invention

The present invention relates to an item of clothing for the treatment of skin and subcutaneous tissue disorders and sports recovery, comprising a tubular body with at least one relatively inelastic part, the or each inelastic part having an inner layer defining an inner face of the inelastic part, said inner layer including a plurality of protruding elements spaced apart from one another.

Description of the Related Art

Such an item of clothing is for example known from EP 1,926,458.

However, the current items of clothing are not fully satisfactory. Indeed, the tubular body is most often completely formed by the inelastic part, as a result of which the item of clothing cannot be adjusted to the part of the patient's body for which the treatment is intended. There is then a risk that the pressure exerted on the part of the patient's body may be excessive or insufficient, resulting in poor treatment for the patient. Furthermore, such items of clothing are not easy to put on, since they do not have sufficient extensibility to make it possible to slide a limb easily inside the tubular body.

BRIEF SUMMARY OF THE INVENTION

One aim of the invention is to allow the adjustment of the item of clothing. Other aims are to allow the adjustment of the pressure exerted by the item of clothing on the patient's body, to make the item of clothing easier to put on, and to ensure homogenous treatment of the part of the body to be treated.

To that end, the invention relates, according to a first aspect, to a tubular body also comprising a relatively inelastic part extending from a first axial end to an opposite axial end of the tubular body and connecting a first edge of the inelastic part to a second edge of the inelastic part, and in that the item of clothing further comprises:
  a relatively inelastic flap having an inner layer defining an inner face of the flap, said inner layer including a plurality of protruding elements spaced apart from one another, the flap being secured to at least part of the first edge of the inelastic part, and
  a device for reversibly attaching the flap to at least part of the second edge of the inelastic part, designed such that the flap overlaps the elastic part when it is attached.

The invention also relates, according to a second aspect, to an item of clothing of the aforementioned type, wherein the tubular body also comprises a plurality of relatively elastic parts, each extending from a first axial end to an opposite axial end of the tubular body and each connecting a first edge of an inelastic part to a second edge of another inelastic part, and in that the item of clothing further comprises, for each elastic part:
  a relatively inelastic flap having an inner layer defining an inner face of the flap, said inner layer including a plurality of protruding elements spaced apart from one another, the flap being secured to at least part of the first edge of the inelastic part, and
  a device for reversibly attaching the flap to at least part of the second edge of the inelastic part, designed such that the flap overlaps the elastic part when it is attached.

Preferably, the elastic and inelastic parts are arranged alternating with one another.

According to specific embodiments of the invention, the item of clothing according to the first or second aspect also has one or more of the following features, considered alone or according to any technically possible combination(s):
  the or each inelastic part and the or each flap each comprise an outer layer made from a relatively inelastic material to which the inner layer is fastened;
  the inner layer is fastened to the outer layer by gluing;
  the outer layer is made from a woven or knitted material;
  the reversible attaching device comprises at least one primary fastening member secured to the flap and at least one secondary fastening member secured to the second edge of the inelastic part, the or each primary fastening member being suitable for cooperating with a respective secondary fastening member so as to allow the attachment of the flap to the second edge of the inelastic part in different positions;
  a device for identifying the position of the flap relative to the second inelastic part edge;
  the identification device comprises a first identifying mark borne by the flap, by the inelastic part, respectively, and a plurality of second identifying marks borne by the inelastic part, by the flap, respectively, each second identifying mark being associated with a unique attaching position of the flap to the second edge, the first identifying mark being designed so as, in each attaching position of the flap to the second edge, to be arranged matching the second identifying mark associated with said position;
  the attaching device is a self-adhesive device;
  the protruding elements comprise pieces of foam, three-dimensional knitted squares, pads filled with liquid, or solid polymer slabs.

BRIEF DESCRIPTION OF THE DRAWINGS

Other features and advantages of the invention will appear upon reading the following description, provided solely as an example, and in reference to the appended drawings, in which.

DETAILED DESCRIPTION OF THE PREFERRED EMBODIMENTS

Figure 1:
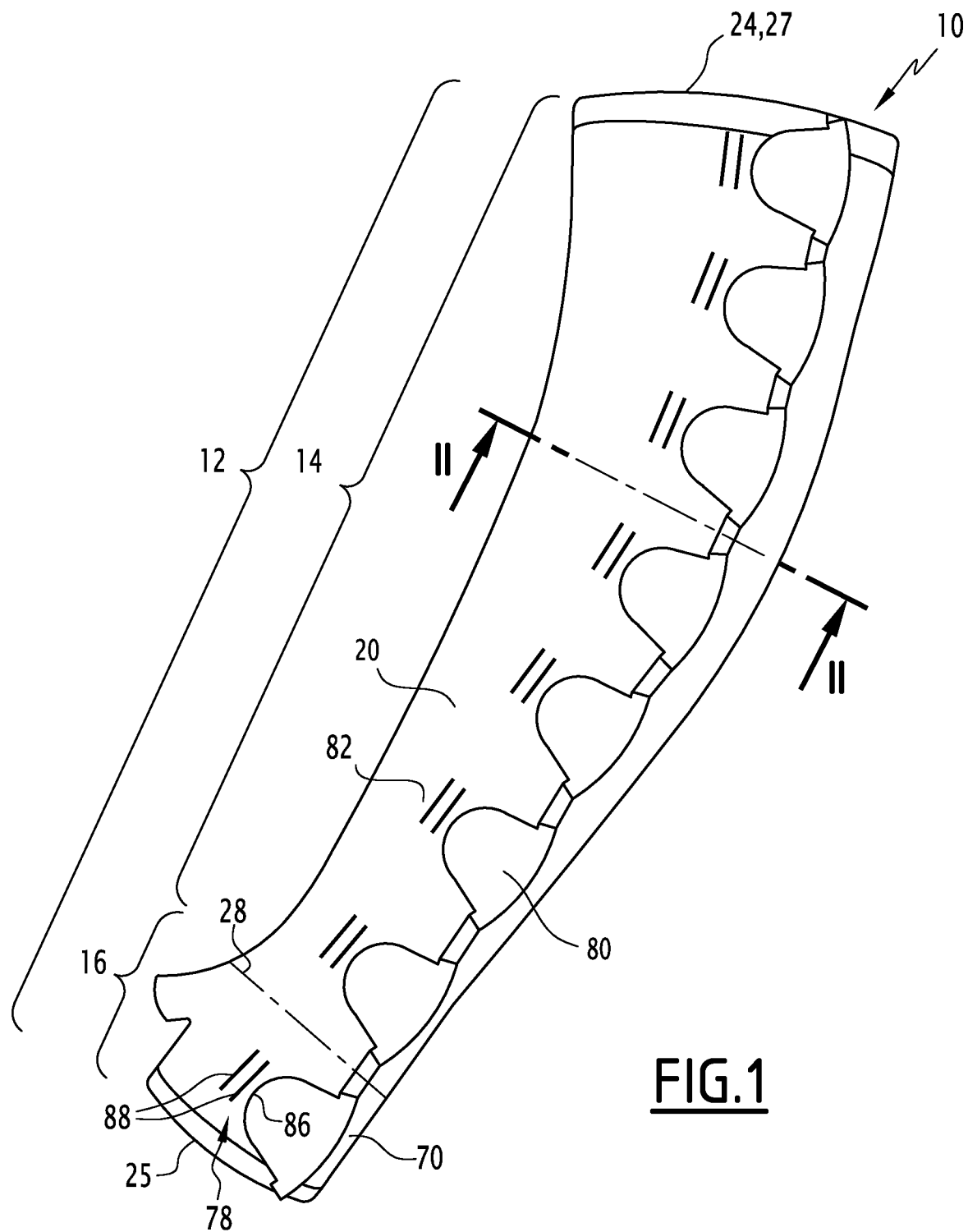
FIG. 1 is a diagrammatic elevation view of an item of clothing according to a first example embodiment of the invention.

The item of clothing 10 shown in FIG. 1 is intended to treat skin and subcutaneous tissue disorders, and in particular to treat various types of the edemas or excessive tissue infiltrations. The item of clothing 10 may also be used for sports recovery after exertion.

In the illustrated example, the item of clothing 10 is a sleeve intended to be placed on the arm of a patient. Alternatively, the item of clothing 10 is a thigh-high stocking, a sock, a glove, a mitten, a panty, a vest, a neck collar or briefs.

The item of clothing 10 comprises a tubular body 12. This tubular body 12 comprises a closed segment 14 and an open segment 16.

The closed 14 and open 16 segments each form a tubular body. They are each open at their respective axial ends. Any cross-section of the closed segment 14 is a closed section. The open segment 16 has a slit (not shown) connecting the axial ends of said segment 16 to one another.

Figure 2:
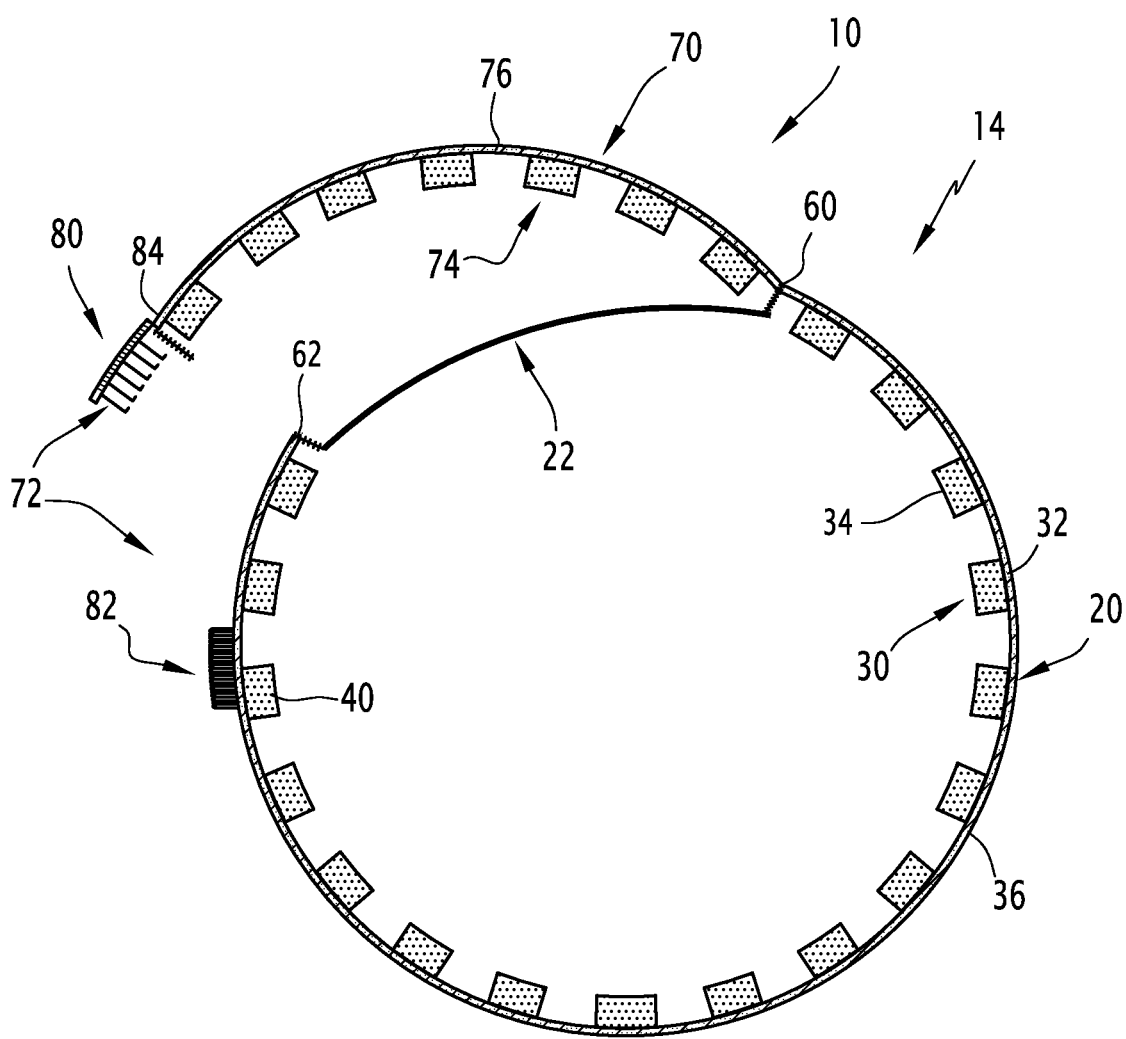
FIG. 2 is a sectional view of the item of clothing of FIG. 1, along a cutting plane marked II-II in FIG. 1, the item of clothing being loosened.
Figure 3:
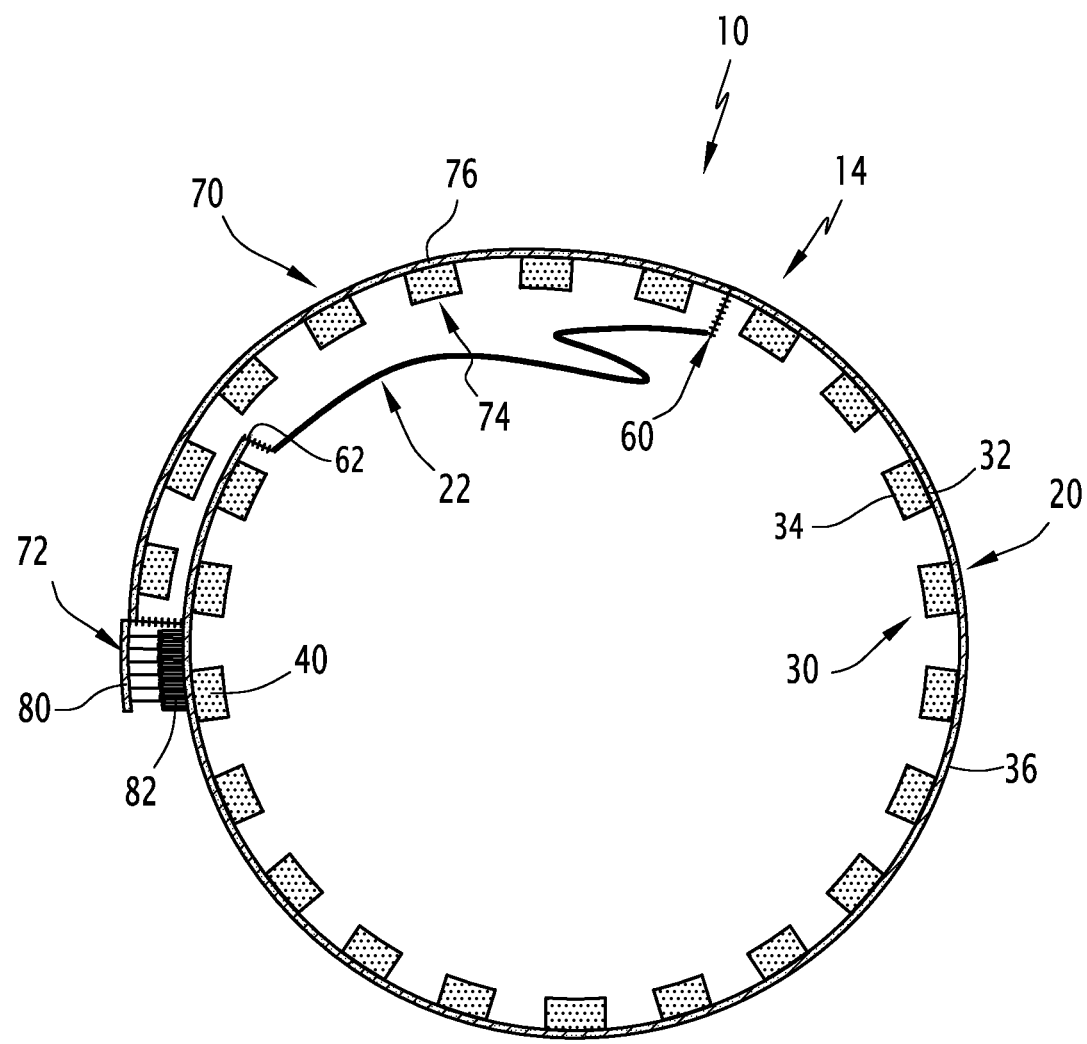
FIG. 3 is a view similar to that of FIG. 2, the item of clothing being tightened.

In reference to FIGS. 2 and 3, the tubular body 12 is formed from an inelastic part 20 and an elastic part 22. Here and below, the terms "elastic" and "inelastic" must be understood as relative terms: the inelastic part 20 is relatively inelastic when it is compared to the elastic part 22, but this does not preclude a certain inherent elasticity of the elastic part 20. Preferably, the difference in elongation between the elastic 22 and inelastic 20 parts, measured according to standard EN 14704-1, is greater than 50% under a force of 5 N/cm.

In reference to FIG. 1, the inelastic part 20 extends from an axial end 24 of the body 12 to the opposite axial end 25. The inelastic part 20 therefore in particular extends from an axial end 27 of the closed segment 14 to the opposite axial end 28.

The elastic part 22 extends exclusively in the closed segment 14. It in particular extends from an axial end 27 of the closed segment 14 to the opposite axial end 28. The open segment 16 is thus formed by only the inelastic part 20.

Returning to FIG. 2, the inelastic part 20 comprises an inner layer 30 and an outer layer 32 fastened to one another. The inner layer 30 is closer to the central axis of the tubular body 12 than the outer layer 32. In particular, the inner layer 30 defines an inner face 34 of the inelastic part 20, oriented toward the central axis of the body 12, and the outer layer 32 defines an outer face 36 of the inelastic part 20, oriented opposite the central axis of the body 12.

The outer layer 32 can be made from a textile, woven, knitted or non-knitted, complexed or non-complexed material, with an elongation preferably below 60% measured according to standard EN 14704-1 under a force of 5 N/cm.

The inner layer 30 is fastened to the outer layer 32, for example by gluing, sewing, welding or the like. It essentially comprises a plurality of protruding elements 40.

In the illustrated example, the protruding elements 40 are foam slabs. Alternatively, the protruding elements 40 are three-dimensional knitted squares, pads filled with a liquid, or solid polymer slabs, for example made from silicone or thermoplastic elastomer (TPE).

In the illustrated example, the protruding elements 40 are placed directly on the outer layer 32 and define the inner face 34 of the inelastic part 20. Alternatively (not shown), the inner layer 30 comprises an inner web, preferably made from a textile material, covering the protruding elements 40 and defining the inner face 34; thus, the patient's skin is protected from direct contact with the protruding elements 40. Also alternatively (not shown), the inner layer 30 comprises, in addition to the inner web, an outer web, also preferably made from a textile material, inserted between the protruding elements 40 and the outer layer 32, the two webs being secured to one another.

Returning to FIGS. 2 and 3, the elastic part 22 connects a first edge 60 of the inelastic part 20 to a second edge 62 opposite said inelastic part 20. It is preferably sewn to said edges 60, 62.

The elastic part 22 preferably has an elongation value comprised between 100 and 200% according to standard EN 14704-1 when subjected to a force of 5 N/cm. It is for example made from Polyamide Elastane jersey knit with an area density of 180 g/m².

Owing to this elastic part 22, the placement of the item of clothing 10 is facilitated by in particular making it possible to enlarge the diameter of the tubular body 12 to slide a limb inside it.

The item of clothing 10 further comprises a flap 70 secured to the first edge 60 of the inelastic part 20, a device 72 for reversibly attaching the flap 70 to the second edge 62 of the inelastic part 20, and a device 78 (FIG. 1) for identifying the position of the flap 70 relative to the second edge 62 of the inelastic part 20.

The flap 70 is relatively inelastic. It comprises an inner layer 74 and an outer layer 76 fastened to one another, the inner layer 74 being identical to the inner layer 30 of the inelastic part 20 and the outer layer 76 being identical to the outer layer 32 of the inelastic part 20. Preferably, the inner layer 74 is an extension of the inner layer 30 of the inelastic part 20 past the first edge 60 and the outer layer 76 is an extension of the outer layer 32 of the inelastic part 20 past the first edge 60; the flap 70 thus constitutes an extension of the inelastic part 20 past its first edge 60.

The attaching device 72 is designed so that, when it is attached, the flap 70 overlaps the elastic part 22 in the closed segment 14 and the slit in the open segment 16. Thus, when the flap 70 is attached, the part of the body to be treated is completely surrounded by the inner layers 30, 74 of the inelastic part 20 and flap 70, which ensures homogenous treatment of that part of the body.

Preferably, the attaching device 72 is also designed so that, when it is attached, the flap 70 partially overlaps the inelastic part 20.

The attaching device 72 comprises a plurality of primary fastening members 80, secured to the flap 70, and a plurality of secondary fastening members 82, secured to the second edge 62 of the inelastic part 20, each primary fastening member 80 being suitable for cooperating with a respective secondary fastening member 82 so as to allow the attachment of the flap 70 to the second edge 62 in different positions. The primary and secondary fastening members 80, 82 are in particular designed to attach the flap 70 to the second edge 62 in a first position, in which the free edge 84 of the flap 70, opposite the end by which the flap 70 is connected to the inelastic part 20, is flush with the second edge 62, and in a second position, in which the free edge 84 of the flap 70 overlaps the second edge 62, as shown in FIG. 3.

It is thus possible to adjust the diameter of the tubular body 12 during the attachment of the flap 70, which makes it possible to adapt the item of clothing 10 to the corpulence of the patient and to adjust the compression force applied on the body by the item of clothing 10.

Each primary fastening member 80 is fastened, for example sewn, glued or welded, to the free edge 84 of the flap 70, and protrudes from that free edge 84 opposite the first edge 60.

In the illustrated example, each secondary fastening member 82 is a part attached on the outer face 36 of the inelastic part 20; it is then sewn, glued or welded to the outer layer 32. Alternatively, the secondary fastening member 82 forms at least part of the outer layer 32.

In the illustrated example, the fastening device 72 is formed by a self-adhesive device, in particular of the loop and hook type (better known under the brand Velcro®). The primary fastening member 80 then preferably includes the hooks and the fastening member 82 includes the loops.

Alternatively (not shown), the fastening device 72 is formed by a loop and strap system, a plastic part, hooks, a snap, or a magnetic gripping system.

Returning to FIG. 1, the identification device 78 comprises a first identifying mark 86 borne by the flap 70 and a plurality of second identifying marks 88 borne by the outer face 36 of the inelastic part 20, each second identifying mark 88 being associated with a respective attaching position of the flap 70 to the second edge 62. The first identifying mark 86 is designed so as, in each attaching position of the flap 70 to the second edge 62, to be positioned matching the second identifying mark 88 associated with said position.

In the illustrated example, the first identifying mark 86 is formed by the free end of the primary fastening member 80 and each second identifying mark 88 is formed by a mark, in particular a line parallel to the edge 62, marked on the secondary fastening member 82. The first identifying mark 86 is then matched with a second identifying mark 88 when it is flush with the mark constituting that second identifying mark 88. Alternatively, each second identifying mark 88 is made by printing, screen printing, sewing, cookie-cutter, or any other method for marking directly on the outer layer 32 of the inelastic part 20.

It is thus possible for the user to easily ascertain the gripping force of the item of clothing 10.

A method for using the item of clothing 10 will now be described, in reference to FIGS. 1 to 3.

The user first puts on the item of clothing 10, the flap 70 then not being attached to the second edge 62 of the inelastic part 20. When the tubular body 12 passes around portions of the body that are wider than the part intended to be treated, the tubular body 12 widens, owing to the elasticity of the elastic part 22. The item of clothing 10 is thus easy to put on.

Once the item of clothing 10 is in place, the user folds down the flap 70 on top of the elastic part 22. He then positions the free end 84 of the flap 70 relative to the second edge 62 of the inelastic part 20 so as to match the first identifying mark 86 of the identification device 78 with a second predetermined identifying mark 88, based on the compression force he wishes to apply to the part of the body to be treated. Once this matching is done, the user attaches the flap 70 to the second edge 62. The user can thus easily adjust the compression force he wishes to apply on the part of the body to be treated.

Figure 4:
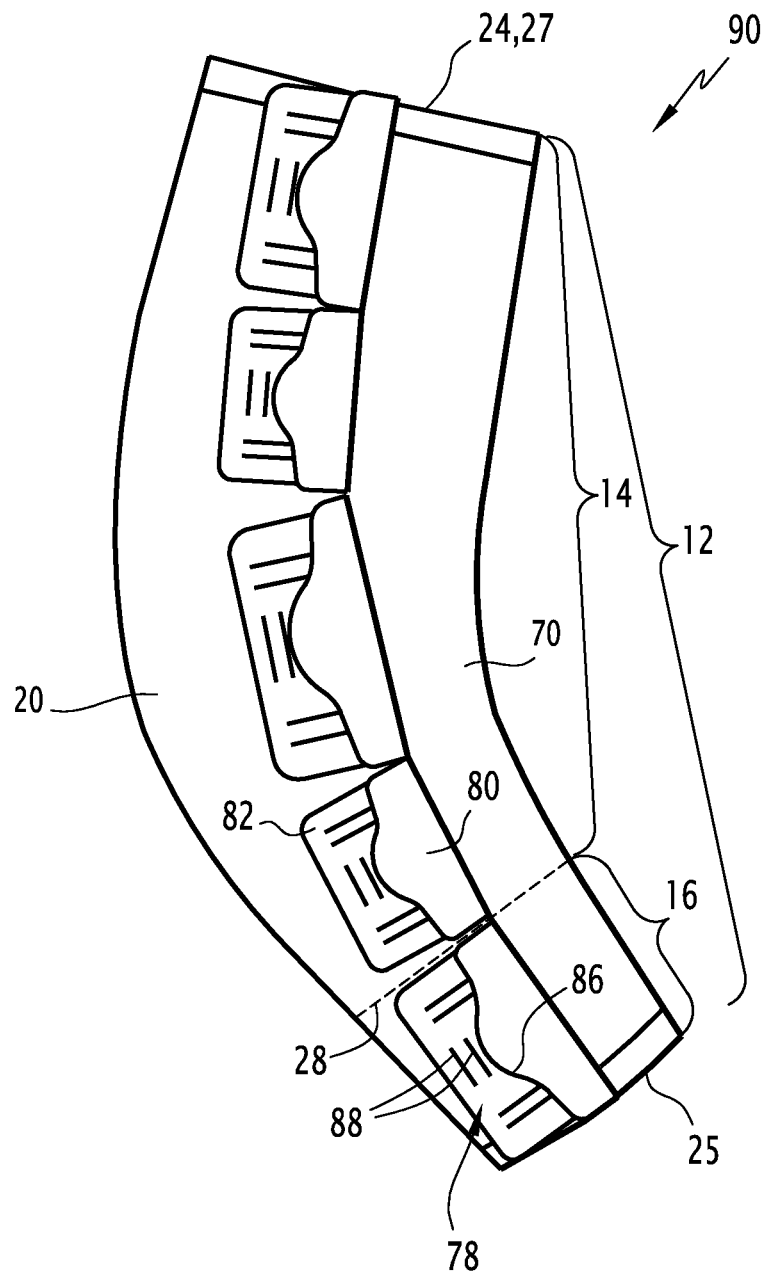
FIG. 4 is a diagrammatic elevation view of an item of clothing according to a second example embodiment of the invention.

The item of clothing 90 of FIG. 4 differs from the item of clothing 10 of FIG. 1 only by the shape of the primary fastening members 80. The same reference signs have been used for elements identical to those of the item of clothing 10.

Figure 5:
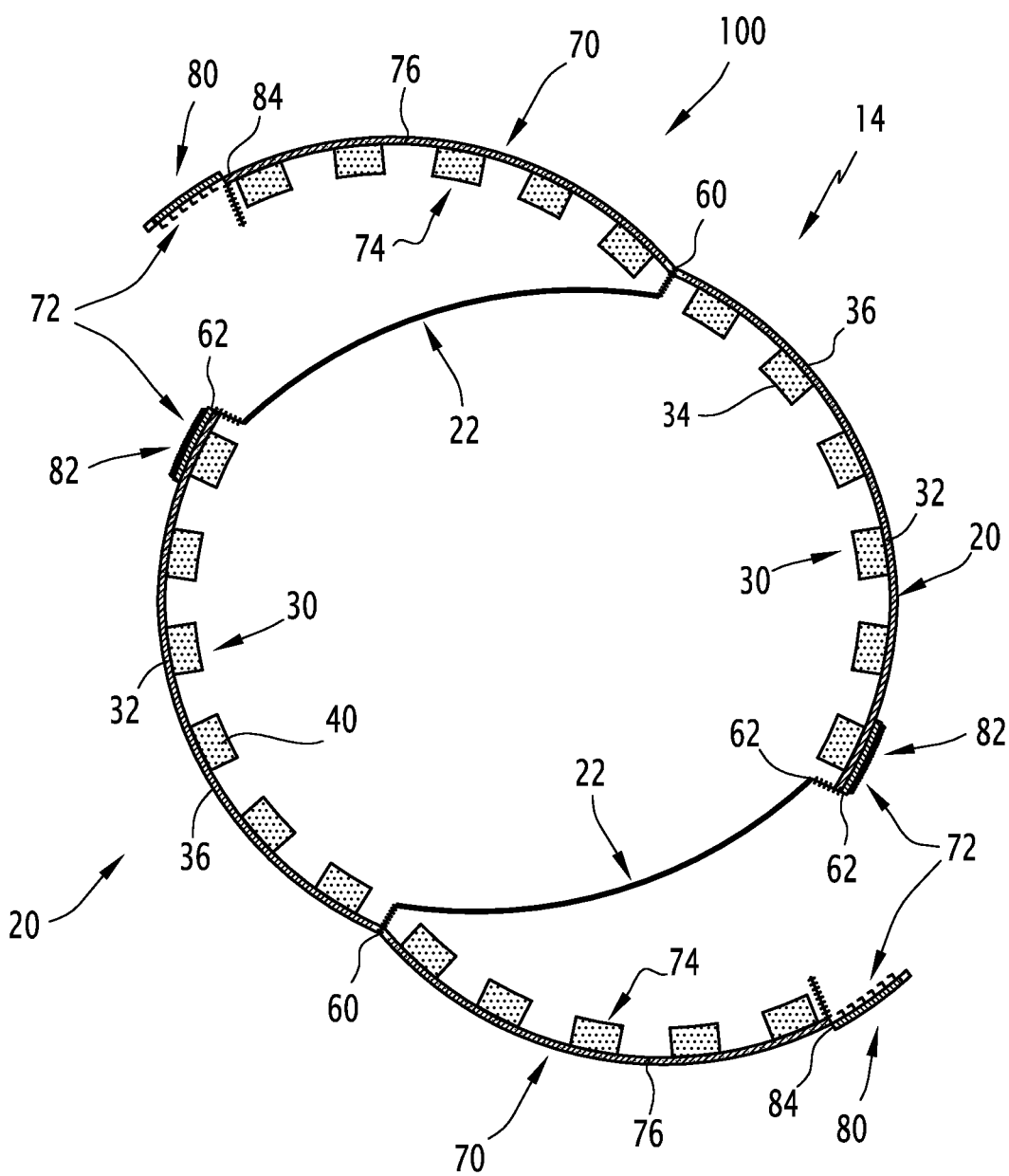
FIG. 5 is a diagrammatic sectional view of an item of clothing according to a third example embodiment of the invention.

The item of clothing 100 of FIG. 5 being largely identical to the item of clothing 10 of FIG. 1, the same reference signs have been used for identical elements. It differs therefrom only in that the tubular body 12 comprises a plurality of inelastic parts 20 spaced apart from one another and a plurality of elastic parts 22 connecting the inelastic parts 20 to one another, and in that it comprises a plurality of flaps 70, each suitable for overlapping a respective elastic part 22 when it is attached. In particular, each elastic part 22 connects a first edge 60 of an inelastic part 20 to a second edge 62 of another inelastic part 20, each flap 70 is secured to a first edge 60 of an inelastic part 20 and is designed to be attached to a second flap 62 of another inelastic part 20, and the elastic 20 and inelastic 22 parts are arranged alternating with one another.

This embodiment is advantageous when the tubular body 12 has a large diameter.

The tubular body 12 has been described as comprising a closed segment and an open segment. It is, however, understood that the invention also applies to any item of clothing comprising only one closed segment, as well as an item of clothing comprising a plurality of closed segments whereof the respective elastic parts are not aligned with one another.

The invention claimed is:

1. An item of clothing for the treatment of skin and subcutaneous tissue disorders and sports recovery, the item of clothing comprising:
    a tubular body having a first axial end and an opposite axial end, the first axial end and the opposite axial end being ends of the tubular body,
    the tubular body including a first part which extends from the first axial end of the tubular body,
    said first part having an inner layer defining an inner face of the first part,
    said inner layer including a plurality of protruding elements spaced apart from one another,
    wherein the tubular body also comprises a second part extending from the first axial end of the tubular body to the opposite axial end of the tubular body and connecting a first edge of the first part to a second edge of the first part,
    the second part being more elastic than the first part,
    a flap constituting an extension of the first part past the first edge of the first part,
    the flap being less elastic than the second part and having an inner layer defining an inner face of the flap,
    said inner layer of the flap including a plurality of the protruding elements spaced apart from one another,
    the flap being secured to at least part of the first edge of the first part, and
    a reversible fastener,
    the flap being reversibly attached to at least part of the second edge of the first part by the reversible fastener, and with the reversible fastener attaching the flap to the at least part of the second edge of the first part, the flap overlaps the entire second part from the first axial end to the opposite axial end,
    the item of clothing having protruding elements that extend inwardly around an entire circumference of the item of clothing, said circumference extending partly on the tubular body and partly on the flap.

2. The item of clothing according to claim 1, wherein the reversible fastener comprises at least one primary fastener secured to the flap and at least one secondary fastener secured to the second edge of the first part, the or each primary fastener being suitable for cooperating with a respective of the at least one secondary fastener so as to allow attachment of the flap to the second edge of the first part in different attaching positions.

3. The item of clothing according to claim 2, wherein each attaching position of the flap relative to the second edge of the first part corresponds to a respective identification mark on the item of clothing.

4. The item of clothing according to claim 3, further comprising a first identifying mark borne by the flap and a plurality of second identifying marks borne by the first part, each second identifying mark being associated with one of the attaching positions of the flap to the second edge, the first identifying mark being designed so that, in each attaching position of the flap to the second edge, the first identifying mark is arranged matching the second identifying mark associated with said attaching position.

5. The item of clothing according to claim 3, further comprising a first identifying mark borne by the first part and a plurality of second identifying marks borne by the flap, each of the second identifying marks being associated with one of the attaching positions of the flap to the second edge, the first identifying mark being designed so that, in each attaching position of the flap to the second edge, the first identifying mark is arranged matching the second identifying mark associated with said attaching position of the second identifying marks.

6. The item of clothing according to claim 1, wherein the first part and the flap each comprise an outer layer made from a material less elastic than the second part, and to which the inner layer of the first part and the flap is fastened.

7. The item of clothing according to claim 6, wherein the outer layer of the first part and the flap is made from a woven or knitted material.

8. The item of clothing according to claim 6, wherein the inner layer of the first part and the flap is fastened to the outer layer of the first part and the flap by gluing.

9. The item of clothing according to claim 1, wherein the reversible fastener is a hook-and-loop fastener.

10. The item of clothing according to claim 1, wherein the protruding elements of each first part and each flap comprise pieces of foam, three-dimensional knitted squares, pads filled with liquid, or solid polymer slabs.

11. An item of clothing for the treatment of skin and subcutaneous tissue disorders and sports recovery, the item of clothing comprising:
    a tubular body with a plurality of first parts spaced apart from one another,
    each of the first parts having an inner layer defining an inner face of said first part,
    each inner layer including a plurality of protruding elements spaced apart from one another,
    wherein the tubular body also comprises a plurality of second parts,
    each of the second parts of the tubular body extending from a first axial end to an opposite axial end of the tubular body,
    each of the second parts of the tubular body connecting a first edge of a first of the first parts to a second edge of a second of the first parts of the tubular body,
    the second parts being more elastic than the first parts,
    the item of clothing further comprises, for each second part of the tubular body,
    a flap and a reversible fastener,
    each flap and each reversible fastener corresponding to one of the first parts,
    each flap constituting an extension of said corresponding first part past the first edge of the first part,
    each flap being less elastic than the second parts and having an inner layer defining an inner face of the flap,
    each inner layer of the flap including a plurality of the protruding elements spaced apart from one another,
    each flap being secured to at least part of the first edge of the corresponding first part, and
    each flap being reversibly attached to at least part of the second edge of the corresponding first part by the reversible fastener, with the reversible fastener attaching the flap to the at least part of the second edge of the corresponding first part, the flap overlapping the entire corresponding second part from the first axial end to the opposite axial end,
    the item of clothing having protruding elements that extend inwardly around an entire circumference of the item of clothing, said circumference extending partly on the tubular body and partly on the flap.

12. The item of clothing according to claim 11, wherein each of the first parts and each of the flaps comprise an outer layer made from a material less elastic than the second parts to which the inner layer of each first part and each flap is fastened.

13. The item of clothing according to claim 12, wherein each inner layer of each first part and each flap is fastened to the outer layer of the outer layers of each first part and each flap by gluing.

14. The item of clothing according to claim 12, wherein the outer layer of each first part and each flap is made from a woven or knitted material.

15. The item of clothing according to claim 11, wherein each reversible fastener comprises at least one primary fastener secured to one of the flaps and at least one secondary fastener secured to the second edge of the corresponding first part, the or each primary fastener being suitable for cooperating with a respective of the at least one secondary fastener so as to allow attachment of each flap to the second edge of the corresponding first part in different attaching positions.

16. The item of clothing according to claim 15, wherein each attaching position of each flap relative to the second edge of the corresponding first part is corresponds to a respective identification mark on the item of clothing.

17. The item of clothing according to claim 16, further comprising a first identifying mark borne by each flap and a plurality of second identifying marks borne by each first part, or a first identifying mark borne by each first part and a plurality of second identifying marks borne by each flap, each second identifying mark being associated with one of the attaching positions of each flap to the second edge of the corresponding first part, the first identifying mark being designed so that, in each attaching position of each flap to the second edge of the corresponding first part, the first identifying mark is arranged matching the second identifying mark associated with said attaching position of the flap to the second edge of the corresponding first part.

18. The item of clothing according to claim 11, wherein the second parts are arranged alternating with one another.

19. The item of clothing according to claim 11, wherein each reversible fastener is a hook-and-loop fastener.

20. The item of clothing according to claim 11, wherein the protruding elements of the relatively first parts and the flaps comprise pieces of foam, three-dimensional knitted squares, pads filled with liquid, or solid polymer slabs.

\* \* \* \* \*